(12) United States Patent
Stevenson et al.

(10) Patent No.: US 7,902,413 B2
(45) Date of Patent: Mar. 8, 2011

(54) AROMATIZATION OF ALKANES USING A GERMANIUM-ZEOLITE CATALYST

(75) Inventors: Scott A. Stevenson, Houston, TX (US); Dustin B. Farmer, Houston, TX (US); Scott F. Mitchell, The Woodlands, TX (US); Gopalakrishnan G. Juttu, Sugar Land, TX (US); Alla K. Khanmamedova, Sugar Land, TX (US); Paul E. Ellis, Sugar Land, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 978 days.

(21) Appl. No.: 11/786,590

(22) Filed: Apr. 12, 2007

(65) Prior Publication Data

US 2008/0255398 A1    Oct. 16, 2008

(51) Int. Cl.
  *C07C 2/76*    (2006.01)
(52) U.S. Cl. .......................................... 585/419; 585/418
(58) Field of Classification Search ................... 585/419, 585/418
See application file for complete search history.

(56) References Cited

U.S. PATENT DOCUMENTS

| | | | |
|---|---|---|---|
| 4,104,320 A | 8/1978 | Bernard et al. |
| 4,417,083 A | 11/1983 | Bernard et al. |
| 4,435,283 A | 3/1984 | Buss et al. |
| 4,517,306 A | 5/1985 | Buss |
| 4,652,360 A | 3/1987 | Dessau |
| 4,867,864 A | 9/1989 | Dessau |
| 5,358,631 A | 10/1994 | Miller et al. |
| 6,063,724 A | 5/2000 | Resasco et al. |
| 6,358,400 B1 | 3/2002 | Bogdan |
| 6,784,333 B2 | 8/2004 | Jittu et al. |
| 7,153,801 B2 | 12/2006 | Wu |

OTHER PUBLICATIONS

Aromatization of Hydrocarbons over Platinum Alkaline Earth Zeolites; T.R. Hughes et al.; Proceedings of 7th International Zeolite Conference, Tokyo; p. 725-732 (1986).
Octane Enhancement by Selective Reforming of Light Paraffins; P.W. Tamm et al.;Catalysis 1987; J.W. Ward (editor); p. 335-353 (1988).
Selective Catalytic Process for Conversion of Light Naphtha to Aromatics;D.V. Law et al.;Energy Progress; vol. 7; No. 4; p. 215-222 (Dec. 1987).
Effect of Sulfur on the Performance and on the Particle Size and Location of Platinum in Pt/K Aromatization . . . ; G.B. McVicker et al.;J. of Catalysis; vol. 139; p. 46-61 (1993).

*Primary Examiner* — Thuan Dinh Dang
(74) *Attorney, Agent, or Firm* — Jim D. Wheelington

(57) ABSTRACT

This invention relates to a process for the aromatization of $C_6$ to $C_{12}$ alkanes, such as hexane, heptane and octane, to aromatics, such as benzene, ethyl benzene, toluene and xylenes, with a germanium-containing zeolite catalyst. The catalyst is a non-acidic aluminum-silicon-germanium zeolite on which a noble metal, such as platinum, has been deposited. The zeolite structure may be of MFI, BEA, MOR, LTL or MTT. The zeolite is made non-acidic by being base-exchanged with an alkali metal or alkaline earth metal, such as cesium, potassium, sodium, rubidium, barium, calcium, magnesium and mixtures thereof, to reduce acidity. The catalyst is sulfur tolerant and may be pretreated with a sulfur compound, i.e., sulfided. The hydrocarbon feed may contain sulfur up to 1000 ppm. The present invention could be applicable to a feedstream which is predominantly paraffinic and/or low in naphthenes. Lowering the hydrogen to hydrocarbon ratio increases conversion and aromatics selectivity.

39 Claims, 1 Drawing Sheet

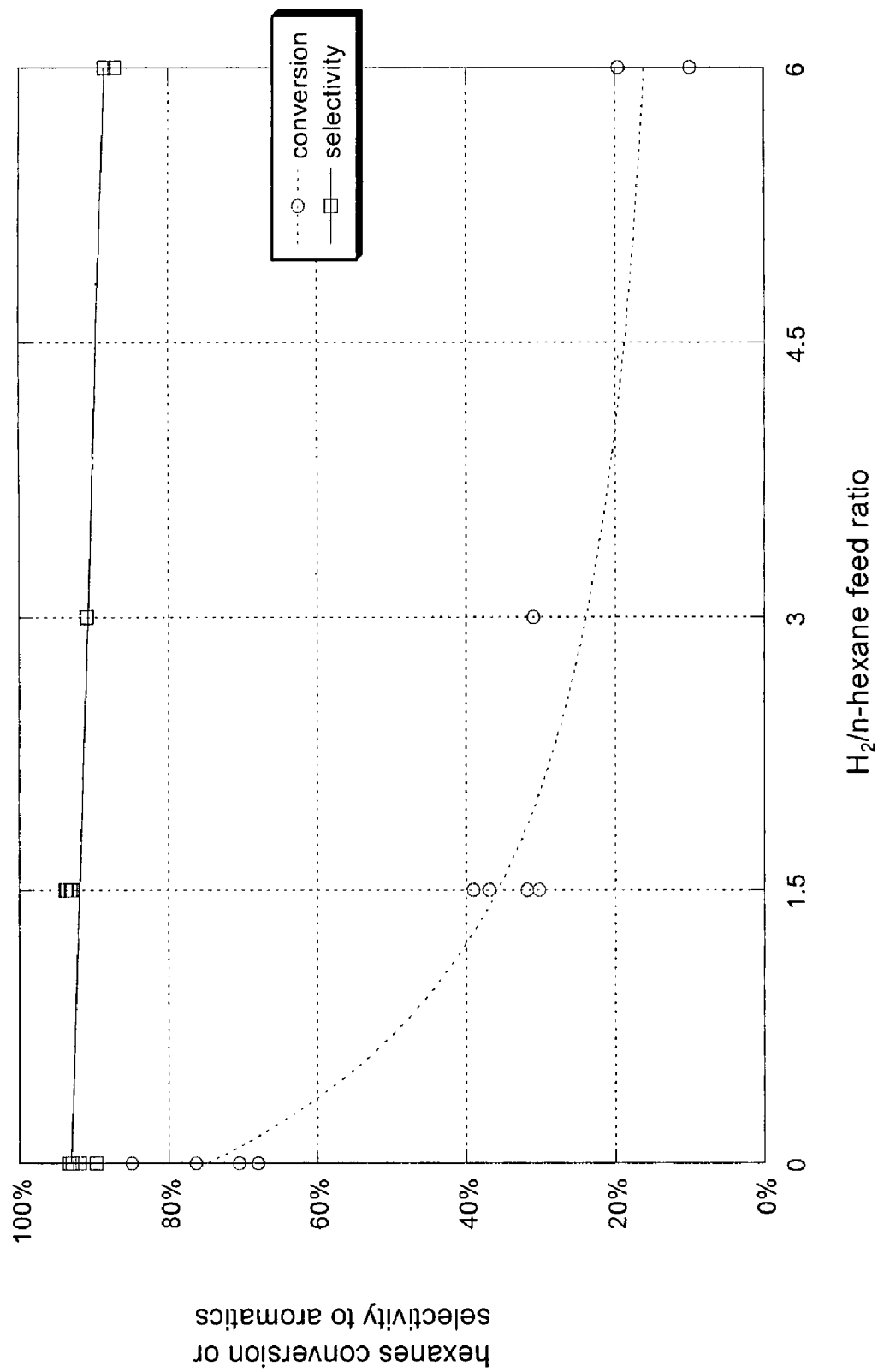
Figure: Variation of selectivity and conversion with feed concentration
Catalyst: 1% Pt/CsGeZSM-5, LHSV = 2.16 hr$^{-1}$, T = 515°C

AROMATIZATION OF ALKANES USING A GERMANIUM-ZEOLITE CATALYST

BACKGROUND OF THE INVENTION

1. Field of the Invention

This invention relates to a process for the aromatization of alkanes to aromatics, specifically use of a base-exchanged zeolite with germanium in the crystalline framework and with a noble metal deposited on the zeolite for the aromatization of alkanes having six to twelve carbon atoms per molecule to produce aromatics, such as benzene, ethyl benzene, toluene and xylene.

2. Description of the Prior Art

Zeolite is a crystalline hydrated aluminosilicate that may also contain other elements in the crystalline framework and/or deposited on its surface. The term "zeolite" includes not only aluminosilicates but substances in which the aluminum is replaced by other trivalent elements and substances in which silicon is replaced by other tetravalent elements. Generally, zeolites are structures of $TO_4$ tetrahedra, which form a three dimensional network by sharing oxygen atoms where T represents tetravalent elements, such as silicon, and trivalent elements, such as aluminum.

A zeolite may be prepared by (a) preparing an aqueous mixture of silicon oxide, aluminum oxide and, optionally, oxides of other trivalent or tetravalent elements; and (b) maintaining said aqueous mixture under crystallization conditions until crystals of said zeolite form. The reaction mixture gel is heated and stirred to form zeolite crystals and then cooled. The zeolite crystals are separated from the gel and are washed, dried and calcined. Elements may be deposited on the zeolite by any means known in the art, for example, metals deposited by impregnation or ion exchange.

Aromatization of alkanes is a multi-step process of dehydrogenation of the alkane, cyclization of the dehydrogenated alkane and aromatization of the cyclized alkane. The catalyst for this process must be multi-functional to have an acceptable conversion and selectivity for the desired products. Zeolites are known catalysts for isomerization, toluene disproportionation, transalkylation, hydrogenation and alkane oligomerization and aromatization. Some zeolite catalysts, especially those containing a Group VIII deposited metal, are susceptible to sulfur poisoning.

U.S. Pat. No. 5,358,631 discloses a process for catalytic reforming or dehydrocyclization of hydrocarbons using a catalyst of a noble metal on an intermediate pore size crystalline silicate having a high silica to alumina ratio (greater than 200) and a relatively low alkali content (less than 6000 ppm). The patented catalyst has sulfur tolerance up to 2 ppm. Low acidity of the catalyst is attained not by using large amounts of alkali but by low aluminum content with low amounts of alkali and/or use of alkaline earth metal, such as magnesium, in the catalyst. Germanium is disclosed as a promoter metal in a conventional reforming catalyst but not in the patented low alkali catalyst.

U.S. Pat. No. 4,652,360 discloses a catalyst of zeolite, preferably ZSM-5 or ZSM-22, on which a Group VIII metal, such as platinum, has been deposited and which has been base-exchanged with Group IA metal cations, such as sodium hydroxide, potassium chloride or cesium hydroxide, to lower or essentially eliminate, the base exchangeable acidic content of the catalyst composition. One example illustrates n-hexane dehydrocyclization using Pt/ZSM-5 catalysts with and without Cs base-exchange treatment. There is no disclosure of germanium in the catalyst.

U.S. Pat. No. 7,153,801 discloses a method of making a catalyst of a large pore zeolite impregnated with platinum and at least one organic ammonium halide of the formula $N(R)_4X$ where X is a halide and R is a substituted or unsubstituted carbon, chain molecule having 1-20 carbon atoms. The ammonium halide may be an acid halide and an ammonium hydride of the formula $N(R')4OH$ where R' is hydrogen or a substituted or unsubstituted carbon chain molecule having 12-20 carbon atoms. The catalyst is a bound potassium L-type zeolite (KL zeolite) used to dehydrocyclize aliphatic hydrocarbons ($C_6$-$C_8$ petroleum naphtha) to produce aromatic hydrocarbons (benzene, toluene and xylenes).

U.S. Pat. No. 4,867,864 discloses a dehydrogenation/dehydrocyclization process with a non-acidic catalyst of zeolite beta and a dehydrogenation/hydrogenation metal, such as platinum. $C_2$-$C_5$ paraffins are dehydrogenated and $C_6$-$C_{12}$ paraffins are dehydrocyclized. The acid content has been reduced by ion exchange of aluminum with Group IA and/or IIA cations, preferably cesium. Hydrogen must be added during dehydrocyclizaton.

Catalysts of platinum deposited on potassium L-zeolite which has been alkaline earth-exchanged (magnesium, calcium, strontium and barium) were disclosed for aromatization of paraffins, especially hexanes and heptanes, in Aromatization of Hydrocarbons over Platinum Alkaline Earth Zeolites, T. R. Hughes, W. C. Buss, P. W. Tamm and R. L. Jacobson, Proceedings of $7^{th}$ International Zeolite Conference, Tokyo, p. 725-732 (1986). This catalyst is extremely sensitive to poisoning by sulfur.

The Aromax® Process selectively converts $C_6$-$C_7$ paraffins to high octane aromatics utilizing a platinum supported L-type zeolite catalyst of low acidity. A relatively high amount of hydrogen co-feed is required. The Pt/KL zeolite catalyst is sulfur-sensitive. The sulfur level in the feed must be controlled to low levels so that the catalyst is not deactivated. Octane Enhancement by Selective Reforming of Light Paraffins, P. W. Tamm, D. H. Mohr, and C. R. Wilson, Catalysis 1987, J. W. Ward (Editor), p. 335-353 (1988). Selective Catalytic Process for Conversion of Light Naphtha to Aromatics, D. V. Law, P. W. Tamm and C. M. Detz, Energy Progress, vol. 7, no. 4, p. 215-222 (December, 1987).

U.S. Pat. No. 4,517,306 discloses a catalyst for reforming paraffins containing at least 6 carbon atoms into corresponding aromatic hydrocarbons. The catalyst is a type L zeolite, an alkaline earth metal and a Group VIII metal which has been reduced with hydrogen. One essential element of the catalyst was the presence of the alkaline earth metal which must be barium, strontium or calcium, preferably barium since it lessens the acidity of the catalyst.

U.S. Pat. No. 4,104,320 discloses a method of dehydrocyclizing aliphatic hydrocarbons in the presence of hydrogen to form corresponding aromatic hydrocarbons with a catalyst of a type L zeolite which has at least 90% alkali metal (sodium, lithium, potassium, rubidium and cesium) exchangeable cations and contains a group VIII dehydrogenating metal and, optionally tin and/or germanium. No example containing germanium was prepared.

U.S. Pat. No. 4,417,083 discloses a process for production of aromatic hydrocarbons from petroleum fractions containing paraffins in the presence of hydrogen and a catalyst of noble metals and, optionally, sulfur deposited on a crystalline zeolitic aluminosilicate, such as zeolite L, having a pore size of larger than 6.5 Angstroms and substituted with more than 90% alkali metal cations, such as potassium. It is disclosed that the catalyst can contain iridium, tin or germanium in the range of 0-1.5% but no example of a catalyst containing germanium is disclosed.

U.S. Pat. No. 4,435,283 discloses a method of dehydrocyclizing alkanes, such as n-hexane, with a catalyst of a large-pore zeolite, such as type L zeolite, a Group VIII metal, such as platinum, and an alkaline earth metal (barium, strontium or calcium). Selectivity for n-hexane dehydrocyclization is greater than 60%. The feedstock is substantially free of sulfur and other known poisons for reforming catalysts.

U.S. Pat. No. 6,063,724 discloses a sulfur-tolerant Pt/KL-zeolite aromatization catalyst. The catalyst has a rare earth ion, such as lanthanum, cerium, praseodymium, neodymium, samarium, europium, gadolinium, terbium, dysprosium, holmium, erbium, thulium, ytterbium or lutetium, incorporated with the L-zeolite. Incorporation of the rare earth ion is by ion exchange, incipient wetness impregnation, chemical vapor deposition or other methods for dispersion of the ions and is after calcination of the L-zeolite.

Deactivation of the Pt/KL-zeolite catalyst in hexane aromatization appears to occur by agglomeration of the platinum and blockage of the zeolite channels. Sulfur accelerates platinum agglomeration and reduces the number of accessible catalytic sites but does not appear to modify activity and selectivity of the catalytic sites. Effect of Sulfur on the Performance and on the Particle Size and Location of Platinum in Pt/K Hexane Aromatization Catalysts, G. B. McVicker, J. L Kao, J. Ziemiak, W. E. Gates, J. L. Robbins, M. M. J. Treacy, S. N. Rice, T. H. Vanderspurt, V. R. Cross and A. K. Ghosh, Journal of Catalysis, vol. 139, p. 46-61 (1993).

It would be advantageous to have a sulfur-tolerant catalyst for aromatization of alkanes with high selectivity to aromatics, such as benzene.

SUMMARY OF THE INVENTION

The catalyst is a non-acidic aluminum-silicon-germanium zeolite on which platinum has been deposited. It is synthesized by preparing a zeolite containing aluminum, silicon and germanium in the framework, depositing platinum on the zeolite and calcining the zeolite. The zeolite is non-acidic by base-exchange with an alkali metal or alkaline earth metal during synthesis of the zeolite or after formation of the crystalline zeolite. Examples of the zeolite structure are MFI, BEA, MOR, LTL or MTT. In one embodiment of the invention the zeolite has a MFI structure. The term "ZSM-5" is used in this Specification to mean a zeolite having a MFI structure. The catalyst is used in a process for aromatization of alkanes by contacting the non-acidic aluminum-silicon-germanium zeolite on which platinum has been deposited with at least one alkane at aromatization conditions and recovering the aromatic product.

BRIEF DESCRIPTION OF THE DRAWINGS

A more complete appreciation of the invention and many of the attendant advantages thereof will be readily understood by reference to the following detailed description when considered in connection with the accompanying drawing:

FIGURE shows the variation of selectivity and conversion with changes in $H_2$/n-hexane feed concentration for a 1% Pt/CsGeZSM-5 catalyst.

DETAILED DESCRIPTION OF THE INVENTION

A catalyst of an aluminum-silicon-germanium zeolite (Ge-zeolite) on which a noble metal has been deposited is base-exchanged with an alkali metal or alkaline earth metal to reduce acidity. The base-exchange may occur before or after the noble metal is deposited. The catalyst is used to convert $C_6$-$C_{12}$ alkanes, such as might be obtained from natural gas condensate, light naphtha, raffinate from aromatics extraction and other refinery or chemical processes, to aromatics, such as benzene, ethyl benzene, toluene and xylenes.

The Ge-zeolite is synthesized from an aqueous gel containing a silica source, a germanium source, an aluminum source and a structure directing agent. The typical technique for synthesizing Ge-zeolites comprises converting an aqueous gel of a silica source, a germanium source and an aluminum source to zeolite crystals by a hydrothermal process, employing a dissolution/recrystallization mechanism. The reaction medium may also contain structuring agents which are incorporated in the microporous space of the zeolite network during crystallization, thus controlling the construction of the network and assisting to stabilize the structure through the interactions with the zeolite components. The reaction mixture gel is heated and stirred to form zeolite crystals and then cooled. The zeolite crystals are separated from the gel and are washed, dried and calcined.

The silicon to aluminum atomic ratio (Si:Al) of the zeolite is preferably greater than 2. One example, without limiting the invention, is a Si:Al atomic ratio in the range from 10 to 200. Another example, without limiting the invention, is a Si:Al atomic ratio in the range from 20 to 150.

The zeolite of the present invention is a medium pore zeolite or large pore zeolite. The term "medium pore" in this Specification should be taken to mean average pore size is in the range from about 5 to about 7 angstroms. The term "large pore" in this Specification should be taken to mean average pore size is in the range from about 7 to about 10 angstroms. It is possible that these ranges could overlap and a particular zeolite might be considered either a medium pore zeolite or a large pore zeolite. Zeolites having an average pore size of less than about 5 angstroms, i.e., a "small pore" zeolite, would not be considered either a medium pore zeolite or a large pore zeolite. A small pore zeolite would not allow molecular diffusion of the molecules of the desired aromatic products, e.g., benzene, ethyl benzene, toluene and xylenes, in its pores and channels. Examples of medium pore zeolites and large pore zeolites, without limiting the invention, are MFI, BEA, LTL, MOR and MTT.

The germanium content of the zeolite is in the range from 0.05% to 10% by weight. One example of germanium content of the zeolite is from 2% to 8% by weight.

The noble metal is deposited on the zeolite by any known method of depositing a metal on a zeolite. Typical methods of depositing a metal on zeolite are ion exchange and impregnation. Deposition of the noble metal results in the noble metal being present not only on the surface of the zeolite but also in the pores and channels of the zeolite. In one example of the present invention, the noble metal is present in the catalyst in the range from 0.05% to 3% by weight. In another example of the present invention, the noble metal is from 0.2% to 0.2% by weight. In another example, the noble metal is from 0.2 to 1.5% by weight. Examples of the noble metal are platinum, palladium, iridium, rhodium and ruthenium.

The zeolite of the present invention is non-acidic. The term "non-acidic" in this Specification should be taken to mean a zeolite which has been base-exchanged with an alkali metal or alkaline earth metal, such as cesium, potassium, sodium, rubidium, barium, calcium, magnesium and mixtures thereof, to reduce acidity. Base-exchange may take place during synthesis of the zeolite with an alkali metal or alkaline earth metal being added as a component of the reaction mixture or may take place with a crystalline zeolite before or after deposition of the noble metal. The zeolite is base-exchanged to the extent that most or all of the cations associated with aluminum are alkali metal or alkaline earth metal. An example of a monovalent base:aluminum molar ratio in the zeolite after base exchange is at least about 0.9.

The zeolite may contain promoters or modifiers as are known in the art. These promoters or modifiers are present in a catalytically effective amount, e.g., about 0.1 weight percent to about 1.0 weight percent.

The catalyst may be supported on or bound with a material, such as a metal oxide; a mixed metal oxide, e.g., oxides of magnesium, aluminum, titanium, zirconium, thorium, silicon, boron or mixtures thereof, a clay, e.g., kaolin or montmorillonite; carbon, e.g., carbon black, graphite, activated carbon, polymers or charcoal; a metal carbide or nitride, e.g., molybdenum carbide, silicon carbide or tungsten nitride; zeolites; a metal oxide hydroxide, e.g., boehmite, to change the physical properties of the catalyst.

The catalyst may contain a reaction product, such as platinum sulfide, that is formed by contact of an element or compound deposited on the surface of the catalyst with a sulfur compound. Non-limiting examples of sulfur compounds are $H_2S$, $C_nH_{2n+2}S$ or $C_nH_{2n+2}S_2$, where n=1-20. The sulfur compound may be added before or during the aromatization reactions of light alkanes, i.e., the catalyst may be pretreated with the sulfur compound or the sulfur compound may be introduced with the hydrocarbon feed when it contacts the catalyst during the aromatization process. A standard sulfiding method that is well known in the art consists in heating in the presence of hydrogen sulfide or a mixture of hydrogen sulfide and hydrogen or nitrogen to a temperature of between 150 and 800° C. or between 250 and 600° C. An example of the amount of sulfur on the catalyst is in the range of from 10 ppm to 0.1 wt. %. The hydrocarbon feed may contain sulfur up to 1000 ppm. In one embodiment of the invention, the hydrocarbon feed contains sulfur from about 1 ppm to about 500 ppm. In another embodiment of the invention, the hydrocarbon feed contains sulfur from about 10 ppm to about 100 ppm.

U.S. Pat. No. 6,784,333, hereby incorporated by reference, discloses a catalyst of an aluminum-silicon germanium zeolite on which platinum has been deposited. The catalyst can be used in aromatization of alkanes, specifically, aromatization of lower alkanes, such as propane. The catalyst may be a MFI zeolite in which germanium is incorporated into the crystalline framework, i.e., Pt/Ge-ZSM-5. The catalyst may be sulfided before or during the aromatization process.

The chemical formula of the catalyst of the present invention may be represented as:

$$M[(SiO_2)(XO_2)_x(YO_2)_y]Z^+_{y/n}$$

where M is a noble metal, such as platinum, palladium, rhodium, iridium, ruthenium or combinations thereof, X is a tetravalent element, Y is aluminum and, optionally, another trivalent element, Z is a cation or combination of cations with a valence of n, such as $H^+$, $Na^+$, $K^+$, $Rb^+$, $Cs^+$, $Ca^{2+}$, $Mg^{2+}$, $Sr^{2+}$ or $Ba^{2+}$, x varies from 0-0.15 and y is 0-0.125. According to the IUPAC recommendations, an example catalyst would be represented as:

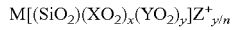

|Cs+Pt|[Si$_{91}$Ge$_4$Al$_1$O$_{192}$]-MFI

The catalyst may be used in a process of aromatization of alkanes, such as alkanes having six to twelve carbon atoms per molecule, to produce aromatics, such as benzene, ethyl benzene, toluene and xylene. The contact between the alkane and the catalyst is at a liquid hourly space velocity in the range between 0.1 and 100 $h^{-1}$, at a temperature in the range between 200 and 600° C. and at a pressure in the range between 5 and 315 psia.

In a process for aromatization of $C_6$-$C_{12}$ alkanes, some embodiments of the present invention have better selectivity to aromatics, are more tolerant to presence of sulfur, have better aromatic yield from acyclic, i.e., linear and branched, paraffins and/or use less hydrogen with respect to catalysts which do not contain germanium. Such developments may produce higher productivity, longer catalyst life, adaptability to certain feedstreams and/or cost reduction in raw material, equipment and process operation. One example of a feedstream to which this catalyst of the present invention would be adaptable would be a feedstream which is predominantly, i.e., greater than about 50% by volume, paraffinic and low, i.e., less than about 20% by volume, in naphthenes. In one embodiment of the present invention, the feedstream contains $C_6$-$C_8$ alkanes, either alone or as components in a mixture, i.e., in a range from 0% to 100% for each $C_6$, $C_7$ and $C_8$ alkane.

The invention having been generally described, the following examples are given as particular embodiments of the invention and to demonstrate the practice and advantages thereof. It is understood that the examples are given by way of illustration and are not intended to limit the specification or the claims to follow in any manner.

CATALYST PREPARATION

Synthesis of Ge-ZSM-5 Zeolite

Solution #1 was made by diluting 15.84 g of 50 wt % NaOH solution with 131.25 g of deionized (DI) water and subsequently dissolving 7.11 g of germanium dioxide. Solution #2 is made by diluting 3.84 g sodium aluminate solution (23.6 wt % alumina and 19.4 wt % sodium oxide) with 153.9 g DI water. Solution #1 was added to 150 g Ludox AS-40 (40 wt % silica in a colloidal state) and vigorously stirred for 10 minutes to obtain a homogeneous mixture. Solution #2 was stirred into this mixture. After 15 minutes of vigorous agitation, 105.42 g of tetra-n-propyl ammonium hydroxide (TPAOH) was added and the mixture was stirred for 60 minutes. Finally, 23.32 g of glacial acetic acid was added to the gel to adjust the pH of the mixture to about 9. This mixture was loaded into a 1 L stainless steel autoclave and heated at 160° C. for 36 hours with stirring. Subsequently, the solids obtained were filtered from the mother liquor and washed with DI water. The solid was calcined at 550° C. for 6 hours in an oven with air flow. The MFI structure of the solid was confirmed by measuring the powder X-Ray diffraction pattern.

Example 1

1% Pt/CsGeZSM-5:

8 grams of GeZSM-5 prepared as described above was washed with 200 ml of aqueous CsNO$_3$ (0.5M) then filtered. The filtrate was then rewashed 3 more times with 0.5M CsNO$_3$ and rinsed with distilled H$_2$O on the final filtering. The zeolite powder was then calcined for 3 hours at 280° C. in air.

Incipient wetness impregnation was carried out by adding drop wise a solution of 0.069 g Pt(NH$_2$)$_4$(NO$_3$)$_2$ dissolved in 1.343 g of deionized water to 3.508 grams of the Cs-exchanged Ge ZSM-5. The material was dried for 1 hour in a 110° C. drying oven then calcined at 280° C. for 3 hours. Elemental analysis gave 39.92 wt % Si, 0.69 wt % Al, 4.14 wt % Ge, 5.03 wt % Cs, and 0.90 wt % Pt.

The catalyst powder was pressed and sized to 20-40 mesh. 0.25 cm$^3$ (0.131 g) of the sized catalyst was mixed with 1.75 cm³ of inert quartz chips and was pretreated at 500° C. for 1 hour in flowing $H_2$. The temperature was then reduced to 460° C. and catalytic testing was started.

Comparative Example 1

1% Pt/CsZSM-5:

12 grams of commercially available ZSM-5 (Zeolyst CBV5524G) was washed with 300 ml of aqueous $CsNO_3$ (0.5M) then filtered. The filtrate was then rewashed 3 more times with 0.5M $CsNO_3$ and rinsed with distilled $H_2O$ on the final filtering. The zeolite powder was then calcined for 3 hours at 280° C. in air.

Incipient wetness impregnation was carried out by adding drop wise a solution of 0.1374 g $Pt(NH_2)_4(NO_3)_2$ dissolved in 6.3507 g of deionized water to 7.0 grams of the Cs-exchanged ZSM-5. The material was dried for 1 hour in a 110° C. drying oven then calcined at 280° C. for 3 hours. Elemental analysis gave 41.54 wt % Si, 1.43 wt % Al, 8.64 wt % Cs, and 0.75 wt % Pt.

The catalyst powder was pressed and sized to 20-40 mesh. 1 cm³ (0.478 g) of the sized catalyst was mixed with 1 ml of inert quartz chips and was pretreated at 500° C. for 1 hour in flowing $H_2$. The temperature was then reduced to 460° C. and catalytic testing was started.

Comparative Example 2

1% Pt/BaZSM-5:

8 grams of commercially available ZSM-5 (Zeolyst CBV5524G) was washed with 150 ml of aqueous $BaNO_3$ (0.25M) then filtered. The filtrate was then rewashed 4 more times with 0.25M $BaNO_3$ and rinsed with distilled $H_2O$ on the final filtering. The zeolite powder was then calcined for 3 hours at 280° C. in air.

Incipient wetness impregnation was carried out by adding drop wise a solution of 0.0362 g $Pt(NH_2)_4(NO_3)_2$ dissolved in 1.17 g of deionized water to 1.8 grams of the Cs-exchanged Ge ZSM-5. The material was dried for 1 hour in a 110° C. drying oven then calcined at 280° C. for 3 hours. Elemental analysis gave 42.75 wt % Si, 1.47 wt % Al, 1.55 wt % Ba, and 1.02 wt % Pt.

The catalyst powder was pressed and sized to 20-40 mesh. 0.25 cm³ (0.122 g) of the sized catalyst was mixed with 1.75 cm³ of inert quartz chips and was pretreated at 500° C. for 1 hour in flowing $H_2$. The temperature was then reduced to 460° C. and catalytic testing was started.

Comparative Example 3

1% Pt/HZSM-5:

Incipient wetness impregnation was carried out by adding drop wise a solution of 0.0701 g $Pt(NH_2)_4(NO_3)_2$ dissolved in 2.2822 g of deionized water to 3.505 grams of commercially available ZSM-5 (Zeolyst CBV5524G). The material was dried for 1 hour in a 110° C. drying oven then calcined at 280° C. for 3 hours.

The catalyst powder was pressed and sized to 20-40 mesh. 0.5 cm³ (0.230 g) of the sized catalyst was mixed with 1.5 cm³ of inert quartz chips and was pretreated at 500° C. for 1 hour in flowing $H_2$. The temperature was then reduced to 460° C. and catalytic testing was started.

CATALYST TESTING

Catalysts prepared by the procedures above were tested as follows: Catalyst particles, mixed with inert quartz chips, were loaded into a ¼" OD plug reactor. n-hexane was vaporized into a stream of flowing hydrogen at a temperature of approximately 150° C. This gas mixture was passed through the reactor, which was maintained at the specified reaction temperature by an external heating jacket. The reaction products were analyzed by gas chromatography. Products ranging in size from methane to dimethylnaphthalene were observed. A variety of $C_6$ isomerization products were observed, including isohexanes (e.g., 2-methylpentane) and olefins (e.g. 1-hexene.) For the purposes of calculating conversion and selectivity, these $C_6$ products were considered to be unreacted. The selectivities reported are calculated as the sum of benzene, toluene, xylenes, and ethyl benzene produced divided by the sum of benzene and all $C_1$-$C_5$ and $C_{7+}$ materials recovered. These selectivities are presented on a molar $C_6$ basis. Activities are for total $C_6$ conversion (excluding isomerization) after 25 hours on stream and are relative to a catalyst producing 50% conversion at 460° C. at a gas hourly space velocity of 5600 $hr^{-1}$. Results are shown in Table 1 below.

TABLE 1

| Catalyst | Activity | Selectivity (460° C.) | Selectivity (480° C.) | Selectivity (500° C.) |
|---|---|---|---|---|
| Example 1 1% Pt/CsGeZSM-5 | 0.34 | 46 | 59 | 78 |
| Example 1(retest) 1% Pt/CsGeZSM-5 | 0.30 | 45 | 54 | 76 |
| Comparative Example 1 1% Pt/CsZSM-5 | 1.90 | 23 | 30 | 43 |
| Comparative Example 2 1% Pt/BaZSM-5 | >15 | 6 | — | — |
| Comparative Example 3 1% Pt/HZSM-5 | >8 | 2 | — | — |

The data in Table 1 show increased selectivity for the germanium-containing ZSM-5 catalyst. The 1% Pt/CsGeZSM-5 catalyst showed a significant increase in selectivity over non-germanium catalysts whether they were non-acidic or not. The data demonstrate improved aromatic selectivity for a germanium-containing ZSM-5 catalyst.

A catalyst made by the procedure of Example 1 was tested with the procedure above at the specified process conditions. Results are shown in Table 2.

TABLE 2

1% Pt/CsGeZSM-5 catalyst, T = 515° C.

| Time on stream (hours) | LHSV ($hr^{-1}$) | $H_2$/n-$C_6$ in feed | conversion (%) | selectivity (%) |
|---|---|---|---|---|
| 111 | 2.16 | 6.0 | 19.6 | 87.1 |
| 118 | 2.16 | 3.0 | 31.0 | 91.0 |
| 124 | 2.16 | 1.5 | 39.0 | 92.9 |
| 141 | 2.16 | 1.5 | 36.9 | 93.1 |
| 143 | 2.16 | 0 | 84.9 | 89.7 |
| 144 | 2.16 | 0 | 76.3 | 92.0 |
| 145 | 2.16 | 0 | 70.5 | 93.0 |
| 146 | 2.16 | 0 | 68.0 | 93.3 |
| 177 | 2.16 | 1.5 | 31.8 | 93.7 |
| 231 | 2.16 | 1.5 | 30.2 | 93.8 |
| 234 | 2.16 | 6.0 | 10.0 | 88.5 |

When the hydrogen to hydrocarbon ratio fed to a base-exchanged Pt/GeZSM-5 is lowered from a hydrogen:alkane molar ratio at about 6:1 to about 0:1, the conversion and selectivity for aromatization increases. Table 2 shows the effect of changing the $H_2$/n-hexane feed ratio for a 1% Pt/Cs-GeZSM-5 catalyst; the same results are shown graphically in FIG. 1. After 111 hours on stream with a $H_2$/n-hexane feed ratio of 6, the conversion at 515° C. and an LHSV of 2.16 hr$^{-1}$ was 19.6% and the selectivity was approximately 87%. Unexpectedly, however, as the $H_2$/n-hexane feed ratio is lowered, the conversion increases sharply, to 31% at a ratio of 3 and to 39% at a ratio of 1.5. In addition, the aromatics selectivity increases to 91% at a ratio of 3 and to 93% at a ratio of 1.5. There is an additional large increase in the conversion when the hydrogen feed is removed completely, but the conversion declines quickly with time on stream. However, when the hydrogen is restored at a ratio of 1.5, the conversion returns to a value only slightly less than that observed before shutting the hydrogen off. Returning to the original ratio of 6 reduces the conversion to only 10% and the selectivity to 88%.

Example 2

1% Pt/KGeZSM-5:

8 grams of GeZSM-5 prepared as described above was washed with 200 ml of aqueous $KNO_3$ (0.5M) then filtered. The filtrate was then rewashed 3 more times with 0.5M $KNO_3$ and rinsed with distilled $H_2O$ on the final filtering. The zeolite powder was then calcined for 3 hours at 280° C. in air.

Incipient wetness impregnation was carried out by adding drop wise a solution of 0.0682 g Pt(NH$_2$)$_4$(NO$_3$)$_2$ dissolved in 1.396 g of deionized water to 3.503 grams of the K-exchanged GeZSM-5. The material was dried for 1 hour in a 110° C. drying oven then calcined at 280° C. for 3 hours. Elemental analysis gave 41.1 wt % Si, 0.73 wt % Al, 4.77 wt % Ge, 1.35 wt % K, and 0.95 wt % Pt.

The catalyst powder was pressed and sized to 20-40 mesh. 0.25 cm$^3$ (0.121 g) of the sized catalyst was mixed with 1.75 cm$^3$ of inert quartz chips and was pretreated at 500° C. for 1 hour in flowing $H_2$. The temperature was then reduced to 460° C. and catalytic testing was started.

Comparative Example 4

1% Pt/KL:

A sample of commercial L-zeolite (Tosoh HSZ500KOA) was obtained in a potassium-exchanged form.

Incipient wetness impregnation was carried out by adding drop wise a solution of 0.393 g Pt(NH$_2$)$_4$(NO$_3$)$_2$ dissolved in 7.5 g of deionized water to 20 grams of the KL-zeolite. The material was dried for 1 hour in a 110° C. drying oven then calcined at 260° C. for 3 hours. Elemental analysis gave 29.2 wt % Si, 9.64 wt % Al, 15.54 wt % K, and 0.94 wt % Pt.

The catalyst powder was pressed and sized to 20-40 mesh. 1 cm$^3$ (1.108 g) of the sized catalyst was mixed with 1 ml of inert quartz chips and was pretreated at 400° C. for 1 hour in flowing $H_2$ before catalytic testing was started.
The catalysts of Example 2 and Comparative Example 4 were tested with the procedure above at the specified process conditions. Results are shown in Table 3.

TABLE 3

| | T = 515° C. 1% Pt for all catalysts | | | |
|---|---|---|---|---|
| Catalyst | LHSV (hr$^{-1}$) | $H_2$/n-$C_6$ in feed | conversion (%) | selectivity (%) |
| Example 2 Pt/KGeZSM-5 | 4.3 | 6.0 | 6.5 | 89.6 |
| | | 1.5 | 17.0 | 91.4 |
| Comparative Example 4 Pt/KL | 4.3 | 6.0 | 20.9 | 89.0 |
| | | 1.5 | 17.5 | 84.2 |

The data in Table 3 show the effect of reducing the hydrogen to hydrocarbon ratio on a germanium-containing ZSM-5 catalyst compared to the L zeolite-based catalyst which does not contain germanium. The 1% Pt/KGeZSM-5 catalyst showed a significant increase in conversion when the $H_2$/n-hexane feed ratio was lowered from 6 to 1.5 and the selectivity also increased. In contrast, the conversion and the selectivity of a 1% Pt/KL catalyst decreased when the $H_2$/n-hexane feed ratio was cut from 6 to 1.5. The data demonstrate improved catalyst performance at lower $H_2$/n-hexane feed ratios for a germanium-containing ZSM-5 catalyst.

The catalysts of Example 1 and Comparative Example 4 were further tested by reducing in a nitrogen/hydrogen mixture, then sulfiding in 1% $H_2S$ in balance nitrogen until breakthrough, about 20-30 minutes. The catalysts were tested using the procedure described above at 460 to 480° C. with a $H_2$/n-hexane feed ratio of six to one. The results are shown in Table 4 below.

TABLE 4

| Catalyst | Activity | Selectivity (460° C.) | Yield | Selectivity (480° C.) | Yield |
|---|---|---|---|---|---|
| Example 1% Pt/CsGeZSM-5 (sulfided) | 0.16 | 36 | 5.76 | 50 | 8 |
| Comparative Example 4 Pt/KL (sulfided) | 0.04 | 82 | 3.28 | 85 | 3.4 |

Sulfiding had a dramatic effect on the activity of the Pt/KL sample; the activity of the presulfided Pt/KL catalyst was about 25% of that obtained with the presulfided Pt/CsGeZSM-5 catalyst. Even though aromatic selectivity for the Pt/KL catalyst was higher than that for the Pt/CsGeZSM-5 catalyst, the overall yield for the Pt/KL catalyst was less. These data demonstrate that a ZSM-5 based catalyst is more sulfur tolerant than a KL-based catalyst.

A catalyst made by the procedure of Example 1 was tested using the procedure described above at the specified process conditions with $H_2$ partially replaced by an inert gas (He) as a diluent. The results are shown in Table 5 below.

TABLE 5

| 1% Pt/CsGeZSM-5 T = 515° C., LHSV = 2.2 hr$^{-1}$ | | | |
|---|---|---|---|
| $H_2$, sccm | He, sccm | conversion, % | selectivity, % |
| 12.5 | 7.5 | 27.1 | 93.6 |
| 10 | 10 | 32.1 | 94.6 |
| 7.5 | 12.5 | 38.1 | 96.1 |
| 5 | 15 | 47.0 | 97.1 |

As can be seen from the data above, increasing the proportion of diluent relative to hydrogen results in increased conversion and selectivity. The diluent could be any inert gas, e.g., He, $N_2$, $CO_2$, $CH_4$, $C_2H_6$ and mixtures thereof. The proportion of diluent relative to hydrogen may be in a molar ratio of hydrogen:inert diluent from about 1:0.6 to about 1:3.

A catalyst made by the procedure of Example 1 was tested using the procedure described above at the specified process conditions with alkanes other than hexane used in a process of aromatization. The results are shown below.
Feed—100% n-heptane
$H_2$/n-$C_7$=0.84
LHSV=5.4 hr-1

Temperature=515° C.
Conversion: 51%
Aromatics Selectivity: 92% (mostly toluene)
Feed—100% n-heptane
$H_2/n-C_7=0.84$
LHSV=2.7 hr-1
Temperature=515° C.
Conversion: 63%
Aromatics Selectivity: 93% (mostly toluene)
Feed—100% n-octane
$H_2/n-C_8=0.93$
LHSV=8.6 hr-1
Temperature=515° C.
Conversion: 35%
Aromatics Selectivity: 88%

| Aromatics Composition: | Ethyl benzene | 53% |
| --- | --- | --- |
| | o-Xylene | 33% |
| | m-Xylene | 10% |
| | p-Xylene | 3% |

Numerous modifications and variations of the present invention are possible in light of the above teachings. It is to be understood that, within the scope of the appended claims, the invention may be practiced other than as specifically described.

What is claimed as new and desired to be secured by Letter of Patent of the United States of America is:

1. A process for the aromatization of hydrocarbons comprising:
   a) contacting a feed containing an alkane of 6 to 12 carbon atoms per molecule at aromatization conditions with at least one catalyst comprising a non-acidic aluminum-silicon-germanium medium pore or large pore zeolite on which a noble metal has been deposited; and
   b) recovering the aromatic product.
2. The process of claim 1 wherein the silicon to aluminum atomic ratio (Si:Al) of the zeolite is greater than 2.
3. The process of claim 2 wherein the silicon to aluminum atomic ratio is in the range from 10 to 200.
4. The process of claim 3 wherein the silicon to aluminum atomic ratio is in the range from 20 to 100.
5. The process of claim 1 wherein the zeolite a medium pore zeolite.
6. The process of claim 5 wherein the average pore size is in the range from about 5 to about 7 angstroms.
7. The process of claim 1 wherein the germanium content of the zeolite is in the range from 0.05% to 10% by weight.
8. The process of claim 7 wherein the germanium content of the zeolite is from 2% to 8% by weight.
9. The process of claim 1 wherein the noble metal is present in the range of from 0.05% to 3%.
10. The process of claim 1 wherein the noble metal is present in the range of from 0.2% to 2%.
11. The process of claim 1 wherein the noble metal is present in the range of from 0.2% to 1.5%.
12. The process of claim 1 wherein the noble metal is platinum, palladium, iridium, rhodium or ruthenium.
13. The process of claim 1 wherein the noble metal is platinum.
14. The process of claim 1 wherein the contact between the alkane and the catalyst is at a liquid hourly space velocity in the range between 0.1 and 100 $h^{-1}$.
15. The process of claim 1 wherein the contact between the alkane and the catalyst is at a temperature in the range between 200 and 600° C.
16. The process of claim 1 wherein the contact between the alkane and the catalyst is at a pressure in the range between 5 and 315 psia.
17. The process of Claim 1 wherein the zeolite has a are MFI, BEA, MOR, LTL or MTT structure.
18. The process of claim 1 wherein the catalyst additionally contains sulfur.
19. The process of claim 1 wherein the catalyst is treated first with hydrogen, second with a sulfur compound; and then again with hydrogen.
20. The process of claim 19 wherein the sulfur compound is $H_2S$, $C_nH_{2n+2}S$ or $C_nH_{2n+2}S_2$, where n =1-20.
21. The process of claim 19 wherein the catalyst is heated in the presence of hydrogen sulfide or a mixture of hydrogen sulfide and hydrogen or nitrogen to a temperature of between 150 and 800° C.
22. The process of claim 21 wherein the temperature is between 250 and 600° C.
23. The process of claim 18 wherein the amount of sulfur on the catalyst is in the range of from 10 ppm to 0.1 wt.%.
24. The process of claim 1 wherein the feed additionally contains sulfur up to 1000 ppm.
25. The process of claim 1 wherein the catalyst is supported or bound.
26. The process of claim 1 wherein the chemical formula of the catalyst is represented as:

$$Pt[(SiO_2)(GeO_2)_x(AlO_2)_y]Z^+_{y/n}$$

where Z is a cation with a valence of n, such as $H^+$, $Na^+$, $K^+$, $Rb^+$, $Cs^+$, $Ca^{2+}$, $Mg^{2+}$, $Sr^{2+}$ or $Ba^{2+}$, x varies from 0-0.15 and y is 0-0.125.

27. The process of claim 1 wherein the catalyst is of the formula:

$$|A^+M|[Si_{91}Ge_4Al_1O_{192}]\text{-MFI}$$

where A is a cesium, potassium, sodium, rubidium, barium, calcium, magnesium and combinations thereof and M is platinum, palladium, rhodium, iridium, ruthenium or combinations thereof.

28. The process of claim 27 wherein A is cesium.
29. The process of claim 27 wherein M is platinum.
30. The process of claim 1 wherein the feed additionally contains hydrogen at a hydrogen:alkane molar ratio from about 6:1 to about 0:1.
31. The process of claim 1 wherein the feed additionally contains hydrogen and an inert diluent.
32. The process of claim 31 wherein the inert diluent is helium, nitrogen, carbon dioxide, methane, ethane and mixtures thereof.
33. The process of claim 32 wherein hydrogen and the inert diluent are present at a molar ratio of hydrogen:inert diluent from about 1:0.6 to about 1:3.
34. The process of claim 1 wherein the zeolite contains modifiers or promoters.
35. The process of claim 1 wherein the feed is predominantly paraffinic and low in naphthenes.
36. The process of claim 1 wherein the feed contains $C_6$-$C_8$ alkanes, either alone or as components in a mixture in a range from 0% to 100% for each $C_6$, $C_7$ and $C_8$ alkane.)

37. The process of claim 1 wherein the zeolite has been base-exchanged with an alkali metal or alkaline earth metal.

38. The process of claim 37 wherein the zeolite has been base-exchanged to the extent that most or all of the cations associated with aluminum are alkali metal or alkaline earth metal.

39. The process of claim 37 wherein the monovalent base:aluminum molar ratio in the zeolite after base exchange is at least about 0.9.

* * * * *